United States Patent [19]

Hiserodt et al.

[11] Patent Number: 5,057,423

[45] Date of Patent: Oct. 15, 1991

[54] METHOD FOR THE PREPARATION OF PURE LAK-ACTIVE LYMPHOCYTES

[75] Inventors: John C. Hiserodt, Pittsburgh, Pa.; Nikola L. Vujanovic, Belgrade, Yugoslavia

[73] Assignee: University of Pittsburgh, Pittsburgh, Pa.

[21] Appl. No.: 134,717

[22] Filed: Dec. 18, 1987

[51] Int. Cl.$^5$ ............... C12N 5/00; A01N 63/00
[52] U.S. Cl. ............... 435/240.23; 435/240.2; 435/240.21; 424/93
[58] Field of Search ............. 435/240.1, 240.23, 240.2, 435/240.25, 240.243; 424/93, 101; 514/21, 2; 530/351

[56] References Cited

U.S. PATENT DOCUMENTS 4,690,915  9/1987  Rosenberg ................... 514/21

OTHER PUBLICATIONS

Abo et al, "Selective Phagocytosis of Gram-Positive Bacteria and Interleukin 1-Like Factor Production by a Subpopulation of Large Granular Lymphocytes", J. Immunology, vol. 136(9), 3189–3197, 5–1986.
Argov et al, "Phorbol Ester-Induced Lymphocyte Adherence: Selective Action on NK Cells", J. Immunology, vol. 134(4), 2215–2222, 1985.
Froelich et al, "Induction of Lymphokine Activated Killer Cells in Serum-Free Medium", J. Immunological Methods, vol. 86, 205–211, 1986.
Lotzová et al, "Induction of NK Cell Activity Against Fresh Human Leukemia in Culture with Interleukin 2," J. Immun., vol. 138, 2718–2727, 4–87.
Stites et al, Basic & Clinical Immunology, 5th ed., Lange Medical Publications, Los Altos, Calif., 1984, pp. 96, 210, 231.
Muul et al, J. Immun. Meth., 88 (1986), 265–275, "Large Scale Production of Human Lymphokine Activated Killer Cells for Use in Adoptive Immunotherapy".
Henkart et al, J. Imm., 137 (1986), 2611–2617, "Cytolytic & Biochemical Properties of Cytoplasmic Granules of Murine Lymphokine-Activated Killer Cells".
Hsieh et al., Gut, 28, 1987, 117–124, "Lysis of Primary Hepatic Tumours by Lymphokine Activated Killer Cells".
Mazumder et al., Cancer Research, vol. 42, 913–918 (Mar. 1982).
Mule et al., The Journal of Immunology, vol. 135, No. 1 646 (Jul. 1985).
Rosenberg et al., The New England Journal of Medicine, vol. 318, No. 15, p. 889 (Apr. 9, 1987).
Rosenberg et al, The New England Journal of Medicine, vol. 313, No. 23, p. 1485 (Dec. 5, 1985).
Mazumder et al, The Journal of Immunology, vol. 130, No. Z, p. 958 (Feb. 1983).
Pistoia et al., Blood, vol. 68, No. 5, p. 1095 (Nov. 1986).

Primary Examiner—Elizabeth C. Weimar
Assistant Examiner—Gail Poulos
Attorney, Agent, or Firm—Choate, Hall & Stewart

[57] ABSTRACT

A method for the preparation of LAK-active lymphocytes; a method of immunotherapy utilizing these LAK-active lymphocytes, relatively homogeneous compositions of large granular lymphocytes, and relatively homogeneous compositions of LAK-active lymphocytes.

21 Claims, 4 Drawing Sheets

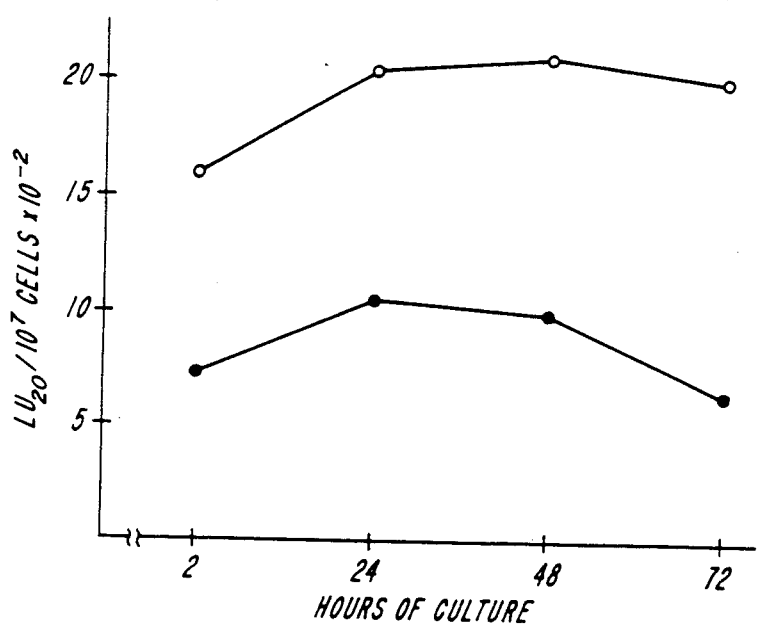
FIG. 1.1
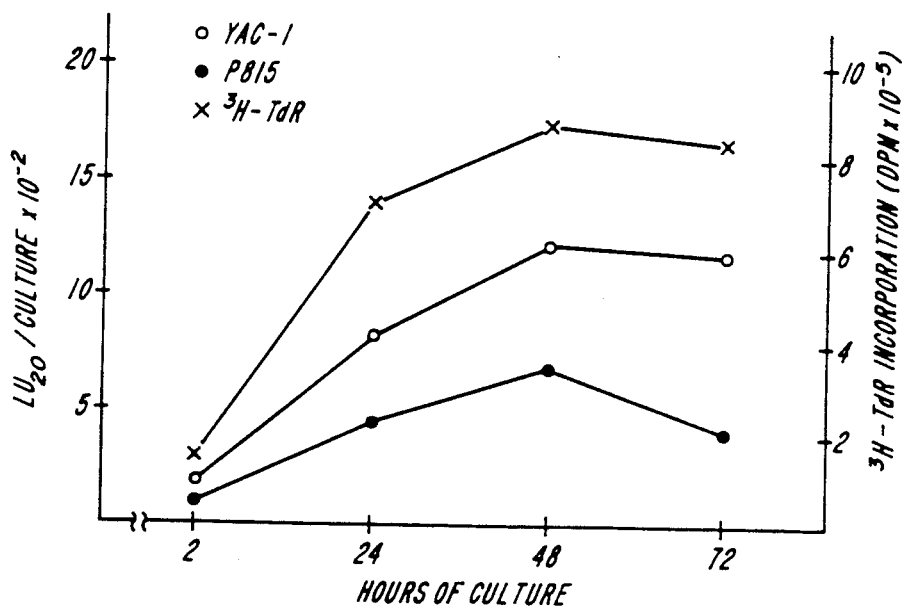
FIG. 1.2

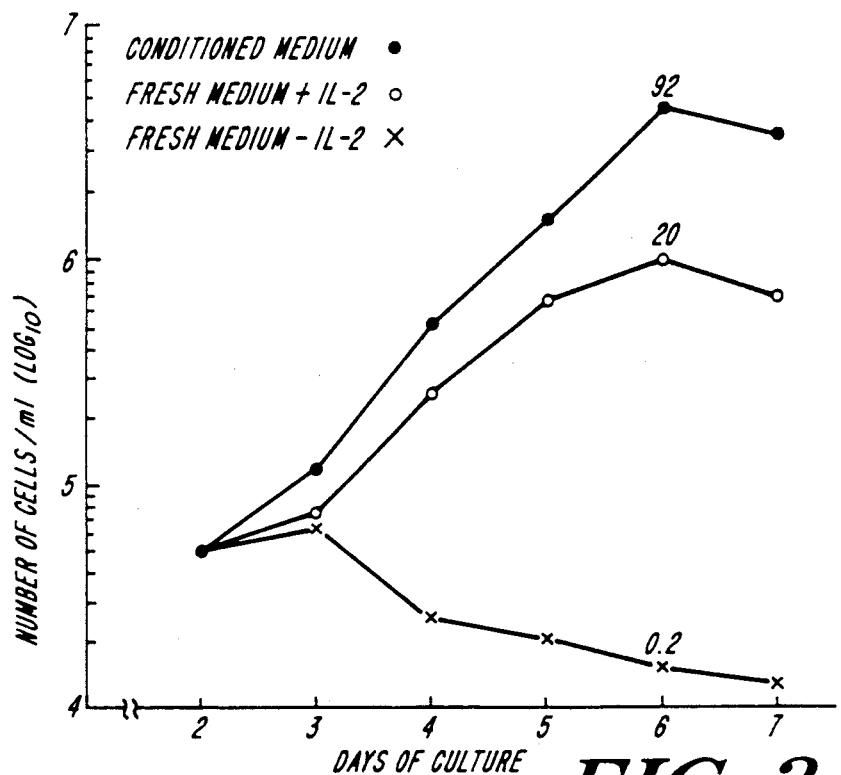
FIG. 3.1
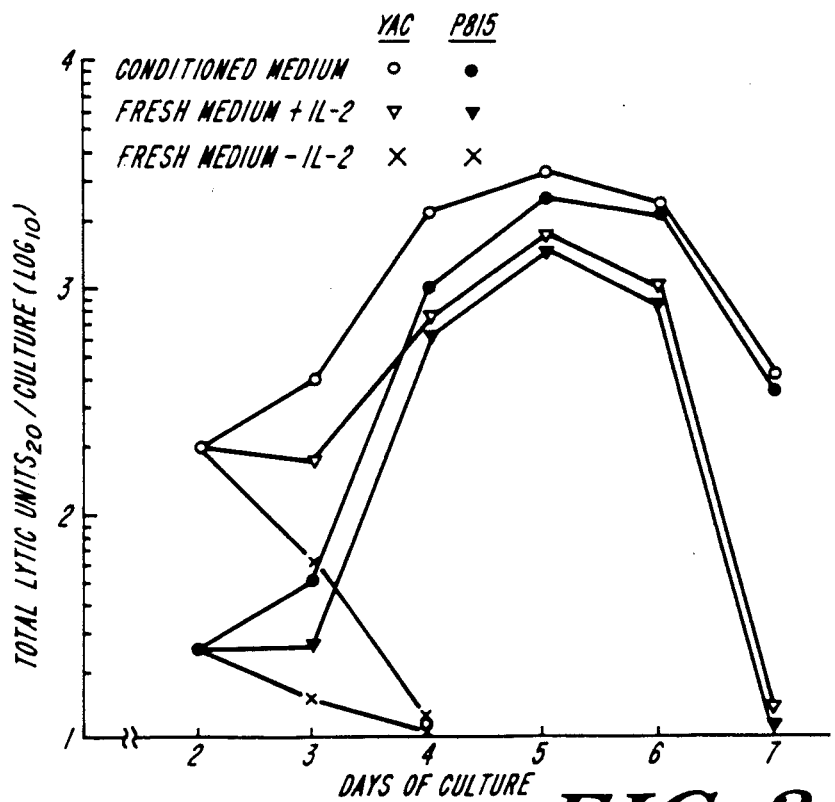
FIG. 3.2

METHOD FOR THE PREPARATION OF PURE LAK-ACTIVE LYMPHOCYTES

ACKNOWLEDGEMENT

The invention described herein was made in part during the course of work under grant Nos. CA-43765 and HL-37638 from the National Institutes of Health.

BACKGROUND OF THE INVENTION

Adoptive immunotherapy constitutes an attempt to manipulate the immune system and involves the administration of immunologically active cells to a subject to enhance the subject's immune response to various deleterious disease states. Cancer and other types of diseases, some of which result in immunodeficiency, have exhibited positive responses to this technique. Adoptive immunotherapy first requires the removal of large numbers of lymphocytes from the subject to be treated or another subject. These cells are then cultured in vitro in immunoenhancing agents such as interleukin-2 (IL-2) or recombinant interleukin-2 (rIL-2) to generate cells having enhanced immunological activity.

One immunologically active cell population responsible for much of the beneficial activity achieved with adoptive immunotherapy is a certain Class of lymphocytes called lymphokine activated killer (LAK) cells which are derived from a progenitor cell population known as natural killer (NK) cells, or large granular lymphocytes (LGL). Both LGL and LAK cells are capable of preferentially lysing or killing certain target cells including tumor cells or virally infected cells.

When these immunologically activated cells are administered to the patient, they act to alleviate the disease state. For example, adoptive immunotherapy has been reported effective in causing regression of a variety of cancers and tumors.

Successful adoptive immunotherapy involves administering large numbers of these cells to an afflicted patient resulting in a difficult and costly procedure. As currently practiced approximately $2 \times 10^{10}$ to $2 \times 10^{11}$ cells are required (assuming the cells have sufficient LAK activity) for a desired response in therapy. It is first problematic to isolate from the normal lymphocyte population the LAK progenitor (LGL) cells; and second to expand these cells to yield large volumes of LAK active lymphocytes. This is particularly true when the LAK progenitor LGL are obtained by leukopheresis from subjects who are to be treated, and who are often already lymphocyte-depleted.

There is accordingly a need for a method which effectively isolates from the normal lymphocyte population the LAK progenitor cells (LGL), and expands them to yield large numbers of LAK active lymphocytes.

SUMMARY OF THE INVENTION

The instant invention comprises a method for isolating LGL from a semi-purified population of lymphocytes comprising culturing the lymphocytes with hIL-2 in plastic or glass containers whereby only the LGL will adhere to plastic or glass.

Instant invention also comprises a method for the expansion and conversion of LGL into LAK active lymphocytes comprising reculturing plastic or glass adherent LGL in hIL-2.

The instant invention also comprises a method of immunotherapy comprising administering to a subject LAK active lymphocytes which have been obtained according to the method of the invention.

The instant invention also comprises a relatively homogeneous composition of large granular lymphocytes as well as a relatively homogeneous population of LAK-active lymphocytes derived from large granular lymphocytes isolated by plastic or glass adherence.

| DEFINITIONS | |
|---|---|
| hIL-2 | human interleukin-2 |
| rhIL-2 | recombinant human interleukin-2 or a mutein form or other modified forms |
| LAK | Lymphokine activated killer |
| LGL | large granular lymphocytes |
| NK | natural killer |
| FCS | fetal calf serum |
| PBS | phosphate buffered saline |
| FITC | fluroscein-isothiocyanate |
| $^3$H-TdR | tritated thymidine |
| F344 Spleen Cells | splenic mononuclear leukocytes from Fisher 344 rats |
| YAC-1 cells | maloney virus induced lymphoma cells which are NK sensitive and used as an indication of NK activity |
| P815 cells | NK resistant mastocytoma cells which are LAK sensitive and used as an indicator of LAK activity |
| LAK medium | tissue culture medium containing a quantity of rIL-2, sufficient to induce LAK activity in susceptible lymphocytes. |
| Conditioned medium | LAK medium in which lymphocytes or other appropriate cells have already been cultured to stimulate LAK activity. |

DESCRIPTION OF DRAWINGS

FIGS. 1.1 and 1.2: Generation of LAK activity from adherent LGL collected at different times after addition of rhIL-2. Nylon wool non-adherent F344 spleen cells were cultured in LAK medium for 2, 24, 48 or 72 hours. At each time point the non-adherent cells were removed and the adherent cells refed with the conditions medium. All cultures were then continued for a total of 5 days. Cytolytic activity on YAC-1 and P815 targets as well as $^3$H-TdR incorporation were determined on day 5. FIG. 1.1: lytic units/$10^7$ cells. FIG. 1.2: Total lytic units/culture and $^3$H-TdR incorporation into DNA.

FIGS. 3.1 and 3.2: Expansion of plastic adherent LGL over a 5 day period. Nylon wool non-adherent F344 spleen cells were cultured for 48 hours in LAK medium. The plastic-adherent cells were collected, and plated at $5 \times 10^4$ cells/ml in 48 hour-conditioned medium or fresh medium with or without rhIL-2. The growth of the cells was then monitored over the next 5 days (FIG. 3.1). The numbers above each curve indicate the fold expansion of the LGL at the peak of expansion without refeeding. FIG. 3.2 shows the expansion of cytotoxic activity against YAC-1 and P815 targets, expressed as total lytic units/culture over the same period.

Figure 2:
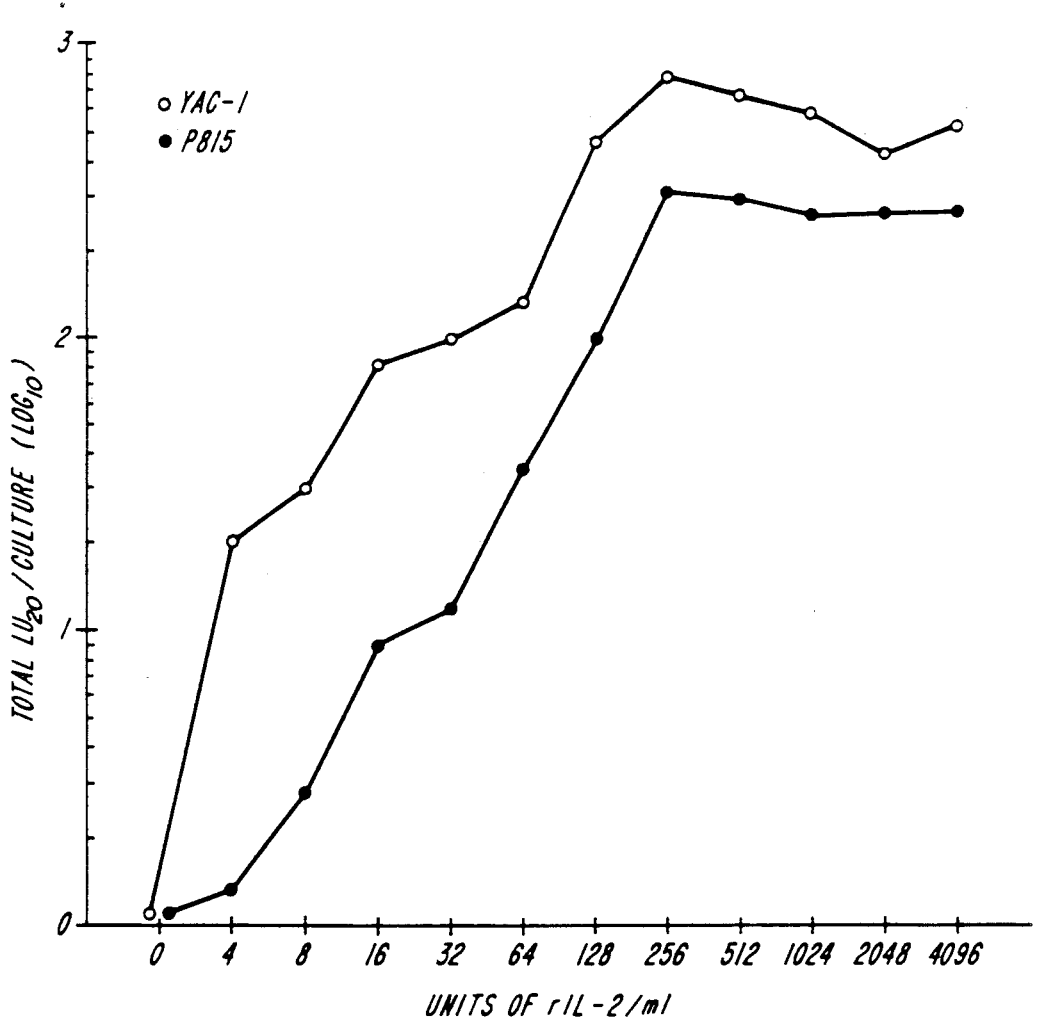
FIG. 2: Interleukin-2 dose-response relationship for the generation of LAK activity from plastic-adherent F344 spleen cells. $20 \times 10^6$ nylon wool non-adherent spleen cells were cultured in T-25 flasks in LAK medium containing various amounts of rhIL-2. After 48 hours the non-adherent cells were removed and the adherent cells refed with the conditioned medium and continued in culture for 3 additional days. Total cytolytic units per culture were then determined for YAC-1 and P815 target cells.

Table 1: Illustrates how LAK activity is generated in purified LGL which have been isolated by their adherence to plastic surfaces.

Table 2: Compares the surface marker phenotype between rhIL-2 induced plastic-adherent LGL and LGL obtained by Percoll Gradients.

Table 3: Compares surface marker phenotype between cells treated according to the method of the invention, Percoll purified LGL, and cells from standard bulk cultures.

Table 4: Comparison of LAK activity generated from plastic adherent LGL, Percoll purified LGL, and cells from standard bulk cultures.

Table 5: Illustrates the production of adherent LAK cells on different plastic and glass bottles.

DETAILED DESCRIPTION

The instant invention comprises the discovery that one of the first responses of LGL or a subset therein after stimulation by hIL-2 is their attachment to plastic or glass surfaces. hIL-2 activated plastic or glass-adherent LGL can expand between 30 up to or greater than 100 fold in 3 to 4 days of culture to generate exceedingly high levels of cells with LAK activity, especially in the presence of Conditioned Medium from activated lymphocytes.

The invention comprises a method for isolating LGL from a semi-purified population of lymphocytes comprising culturing a semi-purified population of lymphocytes with hIL-2 in plastic or glass containers whereby only the LGL will adhere to the plastic or glass.

Preferred is where the hIL-2 is rhIL-2. Also preferred is where the semi-purified population of lymphocytes is cultured from 2 to 72 hours at about 32°-38° C. in standard tissue culture media containing about 100-1200 U/ml rhIL-2.

Particularly preferred is where the semi-purified population of lymphocytes is cultured for about 24, 48 or 72 hours at about 37° C. in standard tissue culture media containing approximately 1000 U/ml rhIL-2.

The purified population of lymphocytes is derived from any heterogeneous cell population obtained from the subject to be treated or another subject. If the cells are derived from tissues, single cell suspensions are prepared utilizing a suitable medium or diluent. Cells may also be derived from peripheral blood by venapuncture and placed into heparinized containers.

The mononuclear cells are first isolated from the heterogeneous population by well known methods, one of which is Ficoll-Hypaque gradient centrifugation as set forth in *Cancer Research*, 42:913-918 (1982); *J. Immunol.*, 130:958-964 (1983) which are hereby incorporated by reference.

If the mononuclear cells are obtained from blood or spleen cells, after Ficoll-Hypaque gradient centrifugation they are then further purified to remove monocytes, macrophages and B cells according to methods well known in the art. For example, the mononuclear cell preparation may be passed over nylon wool columns according to published methods (*The European Journal of Immunology*, 3:645 (1973) which references are hereby incorporated by reference. The nylon wool non-adherent cells constitute the semi-purified population of lymphocytes which may then be further purified according to the method of the invention.

The LGL are then isolated from this purified population of lymphocytes utilizing the plastic or glass adherence phenomenon.

These semi-purified cells are cultured in plastic or glass containers with hIL-2 containing culture media utilizing cell culture methods known in the art. Approximately $10^3$ to $10^7$ viable cells/ml are cultured in the hIL-2 containing tissue culture media. The cells may be cultured for various periods of time from 2 to 72 hours at about 32 to 38° C. in standard tissue culture media containing about 100-1200 U/ml hIL-2. Upon activation by hIL-2, LGL rapidly undergo surface changes which enable their adherence to plastic or glass. Although plastic or glass adherence may be evident after as little as 2 hours of culture in hIL-2, the proliferative ability of 2 hour plastic-adherent cells is limited, hence their expansion and conversion into LAK active lymphocytes is decreased. Plastic or glass adherent cells which have been incubated for about 24 to 72 hours exhibit a greater ability to expand and convert into LAK active lymphocytes (see Table I).

After the requisite incubation periods the tissue culture media is decanted leaving only the cells attached to the plastic or glass surfaces remaining. These cells exhibit a relatively homogeneous population of LGL as evidenced by surface marker tests as set forth in Table 3. The plastic or glass adherent cells should be washed several times with warm culture media or another suitable isotonic solution to remove extraneous non-plastic or glass adherent cells and debris.

The instant invention also comprises a method for the expansion and conversion of LGL into LAK-active lymphocytes comprising reculturing in hIL-2 the plastic or glass adherent LGL which have been isolated according to the method of the invention.

Preferred is where the reculturing media is standard tissue culture media containing 100-1200 U/ml rhIL-2.

Preferred is where the plastic or glass adherent LGL are recultured for 4 to 8 days at 32°-38° C.

Particularly preferred is where the plastic or glass adherent cells are recultured for about 5 to 7 days at about 37° C. in standard tissue culture media containing approximately 1000 U/ml rhIL-2.

The standard tissue culture media used to optimally generate cells with LAK activity may be determined by routine experimentation. Generally from 100-1200 U/ml hIL-2 is necessary and most preferably about 1000 U/ml. Standard cell culture media with the usual proportions of FCS, additives, and antibiotics is generally sufficient and HEPES buffer may be omitted from the media. Standard tissue culture media containing sufficient hIL-2 to generate LAK cells is called LAK media.

Conditioned media may also be used to generate and expand LAK active cells from plastic or glass adherent LGL. Conditioned media is LAK media which has already been used to culture cells. It is made by removing non-adherent cells by centrifugation and filtration.

Conditioned media may be used at 100% concentration or may be diluted 1:1 with fresh LAK media.

The plastic or glass adherent cells are then recultured at about 32°–38° C. for about 4 to 8 days, or most preferably from 5 to 7 days at about 37° C. The non-plastic or glass adherent LGL are removed by decanting the culture medium and the adherent LGL are detached from the plastic or glass by adding several milliliters of an appropriate diluent such as PBS containing EDTA.

This method provides for high levels of expansion (up to 100-fold) of highly purified LAK progenitor cells, thus achieving cultures of relatively homogeneous expanded LAK-active cells in sufficient numbers to be used for therapy or for in vitro experimentation.

The instant invention incorporates the discovery that LGL rapidly undergo surface changes which enable their adherence to plastic or glass. Evidence that plastic or glass adherent cells are LGL/NK cells include the following:

1) the cells express surface markers characteristic of NK cells (see Table 3)
2) the cells initially contain high levels of YAC-1 (but not P815) cytolytic activity.
3) the cells developed LAK cytolytic activity in response to rIL-2.
4) the cells are large granular lymphocytes.

This observation is consistent with previous results in rats, humans and mice which have indicated that the majority of LAK precursor activity is contained within the LGL/NK subset of lymphocytes.

It is known in this art that LGL Can synthesize DNA and proliferate very rapidly in response to hIL-2. Proliferation of adherent LGL was noted as early as 24 hours after culture and reached plateau levels by 48 to 72 hours. (See FIG. 4).

The expansion of LGL/NK cells using this methodology appears superior to standard LAK culture methodology. These cultures generate significantly higher levels of total cytolytic activity per culture and higher levels of LAK activity against several NK-resistant fresh tumor targets. It is likely that this is so because adherent LGL represent only a small percentage of the cells in a non-fractioned lymphocyte population (bulk culture) (around 1–3%) and since these cells are capable of rapid expansion to generate levels of cytolytic activity substantially higher than that seen in bulk cultures.

The instant invention also comprises a method of immunotherapy comprising administering to a subject LAK-active lymphocytes which have been obtained according to the method of the invention.

The cells may be administered alone or in conjunction with one or more immunoenhancing agents such as hIL-2 or other cytokines or lymphokines. If the LAK cells used for immunotherapy are obtained by leukopheresis from the patient to be treated, the patient may be treated with hIL-2 and/or other immunoenhancing agents prior to leukopheresis.

The methods of adoptive immunotherapy utilizing LAK cells either alone or in conjunction with other known immunoenhancing agents are well known in the art. See *The Journal of Immunology*, 135: 1, 646–652 (July 1985); *The New England Journal of Medicine*, 316:15, 889–897 (Apr. 9, 1987); *The New England Journal of Medicine*, 331:23, 1485–1492 (Dec. 5, 1985).

The LAK-active lymphocytes obtained according to the method of the invention may be administered according to any of the known prior art methods including those set forth above.

The present invention will be further described in connection with the following examples which are set forth for purposes of illustration only.

EXAMPLE 1

Illustrated is the isolation and expansion of large granular lymphocytes into LAK-active Cytotoxic lymphocytes.

MATERIALS AND METHODS

Animals: Male Fischer 344 rats (75–100 grams) were purchased from Taconic Farms (Germantown, N.Y.).

Tumor Cells: Routinely, the lysis of the NK-resistant mastocytoma, P815, was used as an indicator of LAK activity. Other targets included two NK-resistant syngeneic rat tumor cells; MADB106 (F344 mammary adenocarcinoma) (8), and CRNK-16 (F344 LGL leukemia). All of these lines were grown in RPMI-1640 medium with 10% FCS and antibiotics. In several cases, fresh tumor explants were used as targets including fresh ascites tumor of CRNK-16 leukemia and fresh solid tumor explants of the MADB106 adenocarcinoma. The NK-sensitive Moloney virus-induced YAC-1 lymphoma was used as the indicator of NK activity.

Interleukin-2: Human recombinant interleukin-2 (rhIL-2) was provided by the Cetus Corporation (Emeryville, Calif.) and contained $1.25 \times 10^6$ units of rhIL-2/mg of protein.

Preparation of Lymphoid Cells: Spleens were aseptically removed and single cell suspensions prepared in RpMI-1640 with 10% FCS. Splenic mononuclear cells were obtained after centrifugation on Ficoll-Hypaque gradients (density - 1.077) at $300 \times g$ for 20 minutes. Peripheral blood was obtained by cardiac puncture into heparinized syringes. Mononuclear cells were then obtained after centrifugation on Ficoll-Hypaque gradients (density = 1.077) at $300 \times g$ for 30 minutes. Spleen or peripheral blood mononuclear leukocytes were routinely passed over nylon wool columns to remove monocytes/macrophages and B cells. Thus, $10^8$ spleen cells in 2 ml of RPMI-1640, 10% FCS, were added to a 10 cc syringe containing 6 grams of sterile nylon wool (Cellular products, Buffalo, NY). The cells were incubated for 1 hour at 37° C. and the nylon wool gently washed (without squeezing) with 20 ml of 37° C. RPMI-1640, 10% FCS. The non-adherent cells were collected, washed and used. By this procedure, the percentage of B cells in the spleen preparations was consistently reduced to less than 2% (by flow cytometric analysis using anti-Ig antibodies) and the percentage of monocyte/macrophages to less than 0.3% (by morphologic analysis of Giemsa-stained cytocentrifuge preparations). In some experiments LGL were purified from the nylon wool non-adherent blood or spleen cells by Percoll density centrifugation, as described by Reynolds et al.; *J. Immunol* 127:282. Briefly, nylon wool non-adherent leukocytes were placed on 4-step Percoll gradients having densities of 48, 52, 56 and 60% Percoll. The gradients were centrifuged at $400 \times g$ for 30 minutes and the LGL were obtained from the 48/58% interface.

Generation of cells with LAK activity

A. Standard Cultures: cells with LAK activity were produced by culture in rhIL-2. Medium conditions for the generation of LAK activity were determined in preliminary experiments and included the following: RPMI-1640 medium (GIBCO) supplemented with 10% heat-inactivated FCS (GIBCO), 2mM glutamine, $5 \times 10^{-5}$M 2-mercaptoethanol, antibiotics (streptomycin/penicillin), (hereafter referred to as LAK medium) containing $10^3$ U/ml rIL-2. Hepes buffer was routinely omitted from the medium. The lymphoid cells were cultured at an optimal density of $2 \times 10^6$ viable cells/ml in LAK medium in 5% $CO_2$/95% air at 37° C.

B. Adherence Cultures: $50 \times 10^6$ nylon wool non-adherent mononuclear leukocytes were cultured in 25 ml of LAK medium (containing 1000 U/ml rhIL-2) in T-75 flasks (Corning, Corning, N.Y.). The cells were cultured for various periods of time (from 2 to 72 hours) at 37° C. after which the non-adherent cells were decanted and the adherent cells washed 3 times with 20 ml of warm (approximately 37° C.) RPMI-1640 containing 2% FCS. The adherent cells then received 25 ml of either fresh LAK medium containing fresh rhIL-2, or the conditioned medium from which they were initially cultured. This conditioned medium was prepared by removing the non-adherent cells by centrifugation and passing the medium through a 0.45 micron millipore filter. Conditioned medium may routinely be used fresh at a 100% concentration, or may also be used diluted 1:1 with fresh medium. This medium could also be stored at $-20°$ C. without loss of growth promoting activity. The cultures were then continued at 37° C. for a total of 5 to 7 days. To remove the adherent LGL, the medium was decanted and 5 ml of 5mM EDTA in PBS was added and the flask scraped with a rubber policeman. A relatively homogeneous population of LAK active lymphocytes as shown by surface marker analysis as set forth in Example 2, was obtained.

EXAMPLE 2

For surface marker analysis, $2 \times 10^5$ lymphocytes obtained from Example 1 were placed in $12 \times 75$ mm glass tubes in 0.1 ml of staining buffer (PBS, PH 7.3, 0.1% sodium azide, 2% FCS). Various antisera or normal sera were added (1:20 to 1:100 final dilution) for 30 minutes at 4° C. The cells were washed twice and resuspended in FITC-labeled F(ab')$_2$ fragments of anti-IgG of the primary antibody (Cappel). After 30 minutes at 4° C., the cells were washed twice, resuspended on 1% paraformaldehyde and analyzed for fluorescence on a FACStar flow cytometer (Becton-Dickinson, Mountain View, Calif.).

A panel of antibodies was used in these studies. These included the mouse monoclonal antibodies OX8 (CD8 ,$\gamma$1), OX19 (CD5,$\gamma$1), OX6 (Ia,$\gamma$1), OX39 [CD25, (IL-2 receptor,$\gamma$1)] all purchased from Accurate Scientific (Westbury, N.Y.). Each of these antibodies was used at 1:100 dilution based on preliminary dose-response titrations. Monoclonal R1-3B3 ($\gamma$2b) (CD5) and was purchased from Wako Chemical Company (Dallas, Tex.) and used at a 1:200 dilution. Rabbit anti-laminin antiserum (R601) and Monoclonal anti-laminin B$_2$ chain (Lam-1) ($\gamma$2b) having reactivity with NK cells was obtained.

Surface marker analysis was performed to determine the relative contribution of lymphocyte subsets to the population of plastic adherent LGL. The data shown in Table 2 indicate that rIL-2-induced plastic-adherent splenic LGL (24 hour adherent cells, 96% LGL) expressed surface markers characteristic of rat NK cells. These cells were OX8(CD8)+, asailo GM$_1$+, and laminin+, but OX19(CD5)−, R1-3B3(CD5)−, We/25(CD4)−, OX39(CD25)−, Ia− and Ig−. A similar marker profile was observed on 48 hour adherent splenic LGL (Table 2). Although the OX6 (Ia) marker was present on a low percentage of 24 hour adherent cells, nearly 50% of these cells expressed this marker at 48 hours. It should be noted that the increased expression of the OX6 (Ia) antigen on 24 and 48 hour adherent LGL indicates that these cells have undergone activation and does not represent monocyte/macrophage contamination. These adherent cells were not phagocytic (for latex beads).

The data in Table 2 indicate that the phenotype of plastic adherent splenic LGL was essentially identical to that of blood LGL purified by percoll gradient centrifugation. The advantage of using the plastic adherence method becomes obvious when the phenotypes of adherent splenic LGL are compared to percoll purified splenic LGL. In this case, only 55% of the percoll purified spleen cells were LGL, with a substantial level of T cell contamination (around 10%).

The phenotype of the LAK effector cells generated from plastic adherent LGL was also determined. These data are presented in Table 3. Forty-eight hour adherent spleen cells were cultured for 3 additional days to expand and generate LAK effector cells. Surface marker analysis revealed these cells expressed high levels of OX8, asailo GM$_1$, laminin and Ia surface markers. Few cells (0–5%) expressed pan T cell markers (OX19, R1-383), helper T-cell markers (W3/25), or B-cell markers (Ig). In addition, the OX39 marker (IL-2 receptor) was expressed on only 9% of the responding adherent LGL, and in relative low intensity. This phenotype was similar to that obtained from percoll-purified peripheral blood LGL after growth in rIL-2 for 5 days. The phenotype of cells present in standard bulk cultures is also shown for comparison.

EXAMPLE 3

The LAK-active lymphocytes of the invention were tested for cytotoxicity as follows:

Cytotoxicity was measured in a standard 4 hour $^{51}$Cr-release microcytotoxicity assay using 96-well, round-bottomed microplates (Costar, Cambridge, Mass.). The target cells were labelled with 100 uCi of Na$_2$$^{51}$CrO$_4$ per $2 \times 10^6$ cells, washed and seeded into 96-well culture dishes at $5 \times 10^3$ cells/well in 50 ul. Suspensions of effector cells were then added to triplicate wells to give various effector:target (E:T) ratios in a final volume of 200 ul. After an additional incubation at 37° C. for 4 hours, 100 ul of supernatant was removed from each well and was counted in a gamma counter to determine experimental release (ER). Spontaneous release (SR) was obtained from wells receiving target cells and medium only, and total release (TR) was obtained from wells receiving 1% Triton X-100. The SR never exceeded 20% of the TR, and in most experiments in ranged between 5 and 15% of the TR. The percent cytotoxicity was calculated by the following formula:

$$\text{Percent cytotoxicity} = \frac{(ER) - (SR)}{(TR) - (SR)} \times 100$$

Lytic units of cytotoxic activity were determined from linear regression curves plotted from various E:T ratios. In all cases, one lytic unit was defined as the number of effector cells required to cause 20% specific $^{51}$Cr release from $5 \times 10^3$ target cells. Total lytic units per culture were calculated by multiplying the lytic Unit$_{20}$ value by the total number of cells in the culture. The results are summarized in Tables 1 and 4.

The representative data in Table 1 show that within 2 hours of culture in rhIL-2, a population of lymphocytes expressing high levels of YAC-1 cytolytic activity (but not P815 cytolytic activity) became attached to the plastic surface. Using spleen cells, the percentage of cells adhering to the plastic was low (about 1-2%) at 2 hours but increased to approximately 4.5% of the input cells by 48 hours (Table 1).

Cytolytic activity against the NK-sensitive YAC-1 target was high when 2 hour adherent cells were tested and continued to increase when the adherent cells were collected and tested at 24 or 48 hours. Cytolytic activity against YAC-1 from 48 hour adherent cells was approximately 40 times higher than that seen with the non-adherent population and approximately 180 times higher than the cytotoxic activity in fresh unactivated, nylon wool non-adherent spleen cells. Cytolytic activity against the P815 target was undetectable with 2 hour adherent cells but was high in 24 hour adherent cells and peaked with 48 hour adherent cells. The data in Table 1 also show that the proliferative activity of adherent LGL was low with 2 hour adherent cells but became marked in 24, 48 and 72 hour adherent cells.

EXAMPLE 4

To determine the optimal time for selecting the adherent LGL for expansion and generation of LAK activity, kinetic experiments were performed. These data are shown in FIG. 2. Adherent splenic LGL were obtained at 2, 24, 48 or 72 hours and cultured in their own conditioned medium for a total of 5 days. Although similar levels of cytotoxicity were generated on a per cell basis (LU 20 per $10^7$ cells) regardless of when the adherent cells were collected, total lytic units per culture were clearly highest from adherent cells collected at 48 hours. The low levels of total lytic units per culture obtained with 2 hour-adherent cells is indicative of the low number of adherent cells obtained at 2 hours as well as their low level of expansion over the next 5 days. 48 hour cultures were chosen.

EXAMPLE 5

Interleukin-2 dose-response relationship for optimal growth of plastic adherent LGL was determined.

Dose-response experiments were conducted to determine the optimal level of rhIL-2 required to generate and expand adherent spleen cells. Thus, $20 \times 10^6$ nylon wool non-adherent spleen cells were placed in different T-25 flasks and cultured in different levels of rIL-2. After 48 hours the adherent cells were collected, refed with their conditioned medium and allowed to grow for an additional 3 days (5 days total). The results of these experiments are shown in FIG. 3. While adherent cells could be generated in as little as 4 units/ml rhIL-2, optimal levels of expansion and generation of total cytolytic activity per culture were obtained in cultures containing at least 100 units/ml rhIL-2. For rats, this is also the optimal rhIL-2 dose range for generating LAK activity in standard bulk cultures.

EXAMPLE 6

Figure 4:
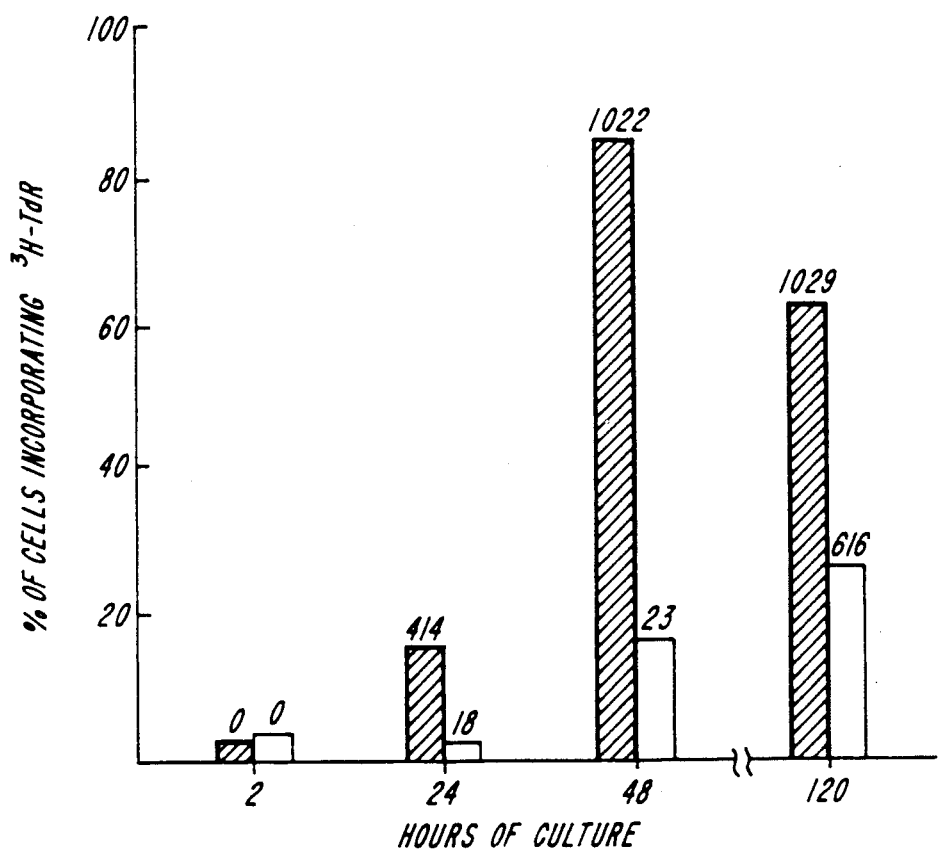
FIG. 4: Kinetics of DNA synthesis in adherent versus non-adherent spleen cells at different times of culture. Using the same protocol as described in FIG. 5, cells showing intense nuclear grain development by autoradiography were scored as positive. 500 cells were counted for each data point. Solid bars represent adherent cells, open bars are the non-adherent cells. The number over the bars indicate the cytotoxic activity lytic units 20 per $10^7$ cells of each population on P815 targets.

The in vitro expansion of rhIL-2 activated plastic-adherent LGL was investigated. The data shown in FIG. 4 indicate that when 48 hour adherent cells were allowed to expand in rhIL-2 for an additional 3-4 days (i.e. 5-6 days of total culture), the expansion indices often reached as much as 90 fold. To determine this, 48 hour adherent cells (97% LGL) were collected then replated at a density of $5 \times 10^4$ cells/ml and allowed to grow for an additional 3-4 days. These cells reached densities between 1.8 and $3.0 \times 10^6$ cells/ml over the next 3 to 4 days (FIG. 1 B, D and FIG. 4A). In some experiments (2 of 6), densities reached as high as $4.5 \times 10^6$ cells/ml (or an expansion of 90 fold). Furthermore, it was noted that when the adherent cells were cultured with the conditioned medium from which they were originally growing the expansion indices were 2 to 3 times higher than when adherent cells were cultured with fresh LAK medium containing fresh rhIL-2 (FIG. 4A). The rapid expansion of LGL was also accompanied by the accumulation of high levels of total cytolytic activity per culture (FIG. 4B).

Although high levels of cellular expansion as well as $^3$H-TdR incorporation were noted, experiments were designed to determine the percentage of cells actively synthesizing DNA. The cumulative data shown in FIG. 4 indicate that by 48 hours in culture, 85% of the adherent cells were synthesizing DNA as detected in a 2 hour pulse of $^3$H-TdR. This was in sharp contrast to the non-adherent cells in which only 18% of the cells were synthesizing DNA.

EXAMPLE 7

Illustrated is that the expansion of plastic adherent LGL generates more efficient broadly-cytotoxic (LAK) killer cells.

Nylon wool non-adherent F344 spleen cells were cultured for 48 hours and the plastic-adherent LGL Collected and cultured for an additional 3 days in conditioned medium. These cells were then tested for cytolytic activity against several tumor cells including fresh explants of 2 different syngeneic NK-resistant targets (MADB106 and CRNK-16). The cytolytic activity of the expanded adherent LGL was compared to bulk cultures of LAK cells generated under standard conditions and to Percoll purified splenic LGL (which contained 55% LGL and at least 10% mature T cells at the initiation of the culture). The data in Table 4 indicate that substantially higher levels of cytolytic (LAK) activity were generated in cultured, purified adherent LGL compared to either standard LAK cultures or partially purified splenic LGL.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

TABLE 1

| | | Generation of LAK Activity from Purified LGL Selected by their Adherence to Plastic Surfaces | | | | | |
|---|---|---|---|---|---|---|---|
| | | | Cells/ml | | | Cytolytic Activity Lytic Units$_{20}$/$10^7$ cells | |
| Group | Hours of Incubation | Cells | $\times 10^{-6}$ | % LGL | Proliferation (DPM $\times 10^{-3}$) | YAC-1 | P815 |
| 1 | 0 | Spleen | 2.00 | 3 | NT | 40 | 0 |

TABLE 1-continued
Generation of LAK Activity from Purified LGL Selected by their Adherence to Plastic Surfaces

| Group | Hours of Incubation | Cells | Cells/ml ×10$^{-6}$ | % LGL | Proliferation (DPM × 10$^{-3}$) | Cytolytic Activity Lytic Units$_{20}$/10$^7$ cells YAC-1 | P815 |
|---|---|---|---|---|---|---|---|
| | 2 | NA | 2.00 | 3 | 2.9 | 102 | 0 |
| | | ADH | 0.02 | 94 | 5.7 | 1008 | 0 |
| | 24 | NA | 2.00 | 3 | 32.1 | 110 | 20 |
| | | ADH | 0.03 | 96 | 144.3 | 5458 | 1105 |
| | 48 | NA | 2.00 | 7 | 32.3 | 195 | 110 |
| | | ADH | 0.09 | 97 | 324.3 | 7266 | 1581 |
| | 72 | NA | 2.00 | 14 | 118.2 | 841 | 145 |
| | | ADH | 0.13 | 97 | 397.4 | 5221 | 948 |
| 2 | 48 | NA | 2.00 | 9 | NT | 123 | 11 |
| | | ADH | .02 | 98 | NT | 2011 | 221 |

Nylon wool non-adherent P344 spleen (Group 1) or peripheral blood (Group 2) mononuclear cells were cultured at $2 \times 10^{-6}$/ml in 1000 U/ml rIL-2 for 2, 24, 48 or 72 hours. At each time point, the adherent (ADH) and non-adherent (NA) cells wre harvested, counted and assayed for proliferation ($^3$H-TdR incorporation into DNA in 4 hours), cytotoxicity against YAC-1 and P815 target cells and the percentage of LGL. The 0 time point represents fresh nylon wool non-adherent spleen cells.

TABLE 2
Surface Marker Phenotype of rIL-2 Induced Adherent LGL Versus LGL Obtained from Percoll Gradients

| Cell Population | % LGL | NK MARKERS OX8 | AsGM1 | laminin | T CELL SUBSET MARKERS OX19 | RI-383 | W3/25 | OX39 | OTHERS Ia | Ig |
|---|---|---|---|---|---|---|---|---|---|---|
| Adherent (24 hr) (spleen) | 96 | 94 | 91 | 74 | 3 | 2 | 2 | 4 | 13 | 2 |
| Adherent (48 hr) (spleen) | 98 | 95 | 97 | 95 | 5 | 4 | 1 | 3 | 46 | 3 |
| Percoll (PBL) | 92 | 96 | 86 | 62 | 4 | 4 | 2 | 2 | 1 | 4 |
| Percoll (spleen) | 55 | 50 | 84 | NT | 9 | 11 | 9 | 3 | NT | 4 |

Nylon wool non-adherent F344 spleen or peripheral blood lymphocytes were obtained and the LGL purified by plastic adherence (24 hr or 48 hr) or Percoll gradient centrifugation. These cells were analyzed for their expression of various surface markers by flow cytometry and LGL were quantitated by Giemsa-stained cytospin preparations (1000 cells counted).

TABLE 3
Phenotype of 5 day expanded cells generated from plastic adherent LGL, Percoll purified LGL or in standard bulk cultures

| LAK cells derived from | % LGL[b] | NK MARKERS OX8 | AsGM1 | laminin | T CELL MARKERS OX19 | RI-383 | W3/25 | OX39 | OTHERS Ia | Ig |
|---|---|---|---|---|---|---|---|---|---|---|
| Adherent LGL[c] | 98 | 80 | 95 | 94 | 4 | 1 | 2 | 9 | 63 | 2 |
| Percoll purified LGL[d] | 95 | 84 | 78 | 68 | 6 | 5 | 6 | NT | 60 | 4 |
| Standard LAK[e] | 42 | 85 | 92 | 54 | 41 | 32 | 4 | 27 | 56 | 12 |

[a]Flow cytometric determination.
[b]Giemsa-stained cytospin preparation (1000 cells counted).
[c]48 hour adherent LGL cultured from nylon wool passed spleen cells. The % LGL in the 48 hour adherent population was 98%. The adherent cells were cultured for an additional 3 days.
[d]Percoll purified peripheral blood LGL. The percent LGL in the purified population was 94% at the initiation of culture. Cells were cultured for 5 days.
[e]Nylon wool non-adherent F344 spleen cells cultured for 5 days.

TABLE 4
LAK Activity Generated from 48 Hour Adherent LGL, Percoll purified LGL and in Standard bulk cultures

| Effector Cells | Cells/ml at day 5 | Cytotoxic Activity (Lytic Units$_{20}$/10$^7$ cells) YAC-1 | P815 | MADB106 | CRNK16 |
|---|---|---|---|---|---|
| Adherent LGL | $1.6 \times 10^6$ | 3564 | 1269 | 1649 | 207 |
| Percoll purified Splenic LGL | $1.8 \times 10^6$ | 1270 | 291 | 1041 | 120 |
| Standard Bulk culture | $2.1 \times 10^6$ | 893 | 273 | 427 | 67 |

Nylon wool non-adherent spleen cells were obtained from F344 rats. LGL were purified by Percoll gradient centrifugation (55% LGL) or by rIL-2 induced plastic adherence (48 hours) (93% LGL). The Percoll purified LGL were cultured in LAK medium for 5 days. The 48 hour adherent LGL were cultured in their conditioned medium for an additional 3 days (for a total of 5 days). Cytotoxicity was tested on YAC-1, P815, and fresh syngeneic MADB106 tumor explants or fresh ascites tumor of CRNK-16 leukemia.

TABLE 5

Production of Adherent-LAK (A-LAK) cells on Different Plastics and glass bottles Donor: F344 Spleen, Nylon-wool passed cells
Culture: $2 \times 10^6$ cells/ml  Falcon T75 Flasks
1000 u/ml rIL-2  Gibco T75
Corning T75
24 Oz prescription bottles

| Condition | No. Cells present in flask at day 5 of culture Total Cells (washed at 2 day) | % Killing at day 5 of culture | | | |
|---|---|---|---|---|---|
| | | YAC-1 Cells | | P815 Cells | |
| | | 10:1 | 2:1 | 10:1 | 2:1 |
| Falcon | | | | | |
| unseparated cells | $29 \times 10^6$ | 36 | 9 | 21 | 6 |
| A-LAK | $18 \times 10^6$ | 79 | 56 | 66 | 34 |
| Gibco | | | | | |
| unseparated cells | $31 \times 10^6$ | 32 | 12 | 24 | 8 |
| A-LAK | $14 \times 10^6$ | 82 | 61 | 69 | 36 |
| Corning | | | | | |
| unseparated cells | $30 \times 10^6$ | 39 | 15 | 25 | 5 |
| A-LAK | $16.6 \times 10^6$ | 79 | 66 | 65 | 39 |
| Bottle | | | | | |
| unseparated cells | $26 \times 10^6$ | 33 | 15 | 22 | 9 |
| A-LAK | $14.9 \times 10^6$ | 81 | 65 | 62 | 41 |

We claim:

1. A method for isolating pure large granular lymphocytes from a semi-purified population of lymphocytes comprising culturing the semi-purified population of lymphocytes in plastic or glass containers with an effective amount of hIL-2 whereby only the large granular lymphocytes will adhere to the interior surface of the plastic or glass containers and harvesting the large granular lymphocytes adhered to the interior surface of the plastic or glass containers.

2. The method of claim 1 wherein the hIL-2 is rhIL-2.

3. The method of claim 2 wherein the semi-purified population of lymphocytes is cultured in plastic containers.

4. The method of claim 3 wherein the lymphocytes are cultured from 2 to 72 hours at about 32°-38° C. in tissue culture media containing about 100-1200 U/ml rhIL-2.

5. The method of claim 4 wherein the lymphocytes are cultured for about 24 to 72 hours.

6. The method of claim 5 wherein the lymphocytes are cultured at about 37° C. in tissue culture media containing about 1000 U/ml rbIL-2.

7. The method of claim 6 wherein the culture medium contains fetal calf serum, antibiotics, glutamine, and mercaptoethanol.

8. The method of claim 7 wherein the density of the cultured purified population of lymphocytes ranges from $10^3$ to $10^7$ viable cells /ml.

9. The method of claim 8 wherein the density of the purified population of cultured lymphocytes is about $2 \times 10^6$ viable cells /ml.

10. The method of claim 9 wherein the plastic containers are petri dishes or falcon flasks.

11. The method of claim 10 wherein the culture media is decanted after culturing and only the plastic adherent large granular lymphocytes remain.

12. A method for the expansion and conversion of large granular lymphocytes into LAK active lymphocytes comprising reculturing in hIL-2 pure large granular lymphocytes which have been isolated by the method of claim 1.

13. The method of claim 12 wherein the large granular lymphocytes have been isolated by plastic adherence.

14. The method of claim 13 wherein the culture media contains 100-1200 U/ml rhIL-2.

15. The method of claim 14 wherein the plastic adherent lymphocytes are recultured for 4 to 8 days at 32°-38° C.

16. The method of claim 15 wherein the plastic adherent lymphocytes are recultured for about 5 to 7 days at about 37° C. in culture media containing approximately 1000 U/ml rhIL-2.

17. The method of claim 16 wherein the culture media is fresh LAK media.

18. The method of claim 16 wherein the media is conditioned media.

19. The method of claim 18 wherein the expanded LAK active lymphocytes are harvested by decanting the excess culture media and scraping the plastic surface to obtain the LAK active cells.

20. The method of claim 19 wherein a suitable buffer is added prior to scraping.

21. The method of claim 20 wherein the buffer is phosphate buffered saline containing EDTA.

* * * * *